(12) United States Patent
Robidoux et al.

(10) Patent No.: US 6,559,304 B1
(45) Date of Patent: May 6, 2003

(54) METHOD FOR SYNTHESIZING CASPASE INHIBITORS

(75) Inventors: Andrea L. C. Robidoux, Andover, MA (US); Jeffrey Douglas Wilson, Boxford, MA (US); Petra Dieterich, Wallingford (GB); Neil Storer, Didcot (GB); Stefania Leonardi, Wallingford (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 67 days.

(21) Appl. No.: 09/688,301

(22) Filed: Oct. 13, 2000

Related U.S. Application Data

(63) Continuation-in-part of application No. 09/136,339, filed on Aug. 19, 1998, now Pat. No. 6,201,118.

(51) Int. Cl.[7] .............................................. C07D 487/04
(52) U.S. Cl. ...................................................... 540/500
(58) Field of Search ........................................ 540/500

(56) References Cited

U.S. PATENT DOCUMENTS

| | | | |
|---|---|---|---|
| 4,512,924 A | 4/1985 | Attwood et al. | |
| 4,692,438 A | 9/1987 | Hassell et al. | |
| 5,716,929 A | 2/1998 | Bemis et al. | |
| 6,204,261 B1 * | 3/2001 | Batchelor | 514/221 |

FOREIGN PATENT DOCUMENTS

| WO | WO 94/11353 | 5/1994 |
|---|---|---|
| WO | WO 97/22619 | 6/1997 |
| WO | WO 00/42061 | 7/2000 |

OTHER PUBLICATIONS

*M. R. Attwood, et al "The Design and Synthesis of the Angiotensin Converting Enzyme Inhibitor Cilazipril and related Bicyclic Compounds" *J. Chem Soc Perkin Trans* pp 1011–1019 (1986).

U. Schmidt, et al "Enantioselective Synthesis of (R) and (S)–Hexahydropyridazine–3–Carboxylic Acid Derivatives", *Synthesis* pp223–229 (1996).

C. P. Decicco, et al "An Improved Asymmetric Synthesis of Piperazic Acids: Retro–Reaction in the Chiral Oxazolidinone Controlled Di–Azo Addition Reaction in a Dipolar Aprotic Medium" *SynLett* pp615–616 (1995).

* cited by examiner

*Primary Examiner*—Robert Gerstl
(74) *Attorney, Agent, or Firm*—Vertex Pharmaceuticals Incorporated; Lisa Dixon

(57) ABSTRACT

The invention relates to a process for simultaneously N(2)-acylating piperazic acid or an ester thereof and forming a bicyclic ring structure. The invention also relates to the use of that process step in a method of synthesizing a bicyclic compound useful as an intermediate for the production of an inhibitor of a caspase, particularly an inhibitor of interleukin-1β converting enzyme ("ICE").

10 Claims, No Drawings

METHOD FOR SYNTHESIZING CASPASE INHIBITORS

CROSS-REFERENCE TO PRIOR APPLICATIONS

This application is a continuation-in-part of U.S. patent application Ser. No. 09/136,339, filed Aug. 19, 1998 now U.S. Pat, No. 6,201,118.

TECHNICAL FIELD OF THE INVENTION

The invention relates to a process for simultaneously N(2)-acylating piperazic acid or an ester thereof and forming a bicyclic ring structure. The invention also relates to the use of that process step in a method of synthesizing a bicyclic compound useful as an intermediate for the production of an inhibitor of a caspase, particularly an inhibitor of interleukin-1β converting enzyme ("ICE").

BACKGROUND OF THE INVENTION

Compounds containing a bicyclic aza-containing ring systems have been prepared as conformationally restricted dipeptide surrogates for a variety of medically important compounds. In particular, such ring systems are present in angiotensin converting enzyme (ACE) inhibitors, such as Cilazapril®, and in caspase inhibitors, such as inhibitors of interleukin-1β converting enzyme (ICE).

Current methods for synthesizing compounds containing these byciclic aza-containing ring systems have many disadvantages. The typical methods of forming this ring system have been described [EP 94,095, WO 95/35308, WO 97/22619, U.S. Pat. Nos. 5,656,627, 5,716,929 and 5,756,486 and J. P. Kim, et al., Tetrahedron Letters, 38, pp. 4935–4938 (1997)].

These methods involve multiple steps wherein an N(1)-protected piperazate must be provided. An appropriately protected amino acid, usually a γ-ester of glutamic acid, is coupled to the piperazate. After deprotection, the bicyclic system is then formed via an acid chloride coupling at the N(1) position.

The main disadvantages to such methods are the use of expensive reagents and the number of steps required for protection and deprotection making the overall process extremely time consuming. Moreover, these methods are often useful for research purposes but are not amenable to large scale production.

In order to be more commercially feasible, it would be desirable to produce compounds containing a byciclic aza-containing ring system in an easier, less expensive manner than has been previously described.

SUMMARY OF THE INVENTION

Applicant has solved this problem by providing a new method of simultaneously N(2)-acylating an N(1)-protected piperazic acid or an ester thereof and creating a bicyclic ring structure comprising that acylated piperazic acid or ester. Until now, formation of said bicylcic compound had not been achieved via N(2)-acylation.

This method involves the formation of the desired bicyclic system in two simple steps. This method also utilizes inexpensive reagents, require no selective protection/deprotection and is amenable to large scale production. Moreover, this method produces very little contaminating by-products. And this method preserves chirality between the N(1)-protected piperazic acid or an ester thereof and the resulting byciclic aza-containing ring system.

This method is particularly useful for producing an intermediate that may be subsequently converted into a caspase inhibitor, particularly an inhibitor of ICE, through additional steps known in the art.

DETAILED DESCRIPTION OF THE INVENTION

The following abbreviations are used throughout this application:

t-Bu=tert-butyl
Et=ethyl
Cbz=carboxybenzyl
DMF=N,N-dimethylformamide
THF=tetrahydrofuran
MTBE=methyl tert-butyl ether
DCC=dicyclohexylcarbodiimide
EDC=1-(3-Dimethylaminopropyl)-3-ethylcarbodiimide hydrochloride
Ac=acetyl.
DBU=1,8-Diazabicyclo[5.4.0]undec-7-ene
Fmoc=9-Fluorenylmethoxycarbonyl According to one embodiment, the invention provides a process for converting compound G to compound H:

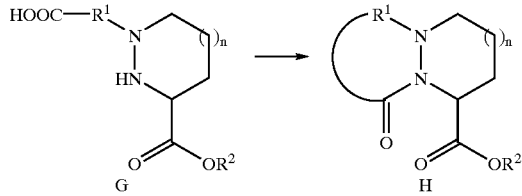

wherein:

$R^1$ is a $C_{2-4}$ straight chain alkyl substituted at the carbon alpha to the COOH moiety with $N(R^4)(R^4)$, $NO_2$ or $N_3$ and optionally substituted at any other carbon with one or more substituents independently selected from $C_{1-6}$ straight or branched alkyl, $C_{2-4}$ straight or branched alkenyl or alkynyl, O—[$C_{1-6}$ straight or branched alkyl], O—[$C_{2-6}$ straight or branched alkenyl or alkynyl], oxo, or halo; wherein each $R^4$ is independently selected from H or an amino protecting group, with the proviso that both $R^4$ are not simultaneously hydrogen;

$R^2$ is selected from hydrogen, $C_{1-6}$ straight or branched alkyl, $C_{2-6}$ straight or branched alkenyl or alkynyl, or Ar, wherein said alkyl, alkenyl or alkynyl is optionally substituted with Ar; wherein Ar is a saturated, partially saturated or unsaturated monocyclic or bicyclic ring structure, wherein each ring contains 5 to 7 ring atoms and each ring optionally contains from 1 to 3 heteroatoms selected from O, N and S; and Ar is optionally substituted at one or more ring atoms with one or more substituents independently selected from $C_{1-6}$ straight or branched alkyl, $C_{2-6}$ straight or branched alkenyl or alkynyl, O—[$C_{1-6}$ straight or branched alkyl], O—[$C_{2-6}$ straight or branched alkenyl or alkynyl], oxo, halo, $NO_2$, $N(R_4)(R_4)$, or CN;

n is 0 or 1;

any substitutable ring carbon is optionally substituted by $Q_1$; wherein each $Q_1$ is independently selected from —$Ar_1$, —$T_1$—$R_9$, or $(CH_2)_{1-3}$—$T_1$—$R_9$; provided that when —$Ar_1$ is substituted with a $Q_1$ which comprises one or more additional —$Ar_1$ groups, said additional —$Ar_1$ groups are not substituted with $Q_1$; wherein Ar$_1$ is a saturated, partially saturated or unsaturated monocyclic or bicyclic ring structure, wherein each ring contains 5 to 7 ring atoms and each ring optionally contains from 1 to 3 heteroatoms selected from O, N and S; and wherein each Ar$_1$ is optionally singly or multiply substituted at any ring atom by —N(R$_9$)(R$_9$), halo, —NO$_2$, —CN, =O, —OH, -perfluoro C$_{1-3}$ alkyl,

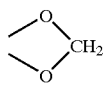

or —Q$_1$;

wherein each R$_9$ is a C$_{1-6}$ straight or branched alkyl group optionally substituted with one or more substituents independently selected from —F, =O or Ar$_1$, wherein any R$_9$ may be substituted with a maximum of two Ar$_1$;

T$_1$ is selected from a valence bond, —CH=CH—, —O—, —S—, —SO—, —SO$_2$—, —NR$_{10}$—, —NR$_{10}$—C(O)—, —C(O)—, —O—C(O)—, —C(O)—O—, —C(O)—NR$_{10}$—, O—C(O)—NR$_{10}$—, —NR$_{10}$—C(O)—O—, —NR$_{10}$—C(O)—NR$_{10}$—, —S(O)$_2$—NR$_{10}$—, —NR$_{10}$—S(O)$_2$—, or —NR$_{10}$—S(O)$_2$—NR$_{10}$—; and each R$_{10}$ is independently selected from —H or C$_{1-6}$ straight or branched alkyl;

The term "amino protecting group", as used herein, means a moiety that prevents chemical reactions from occurring on the nitrogen atom to which that protecting group is attached. An amino protecting group must also be removable by a chemical reaction. Amino protecting groups that are acid cleavable include t-butoxycarbonyl. Examples of amino protecting groups that are base cleavable include Fmoc and alkyl carbamates. Amino protecting groups that are cleaved by hydrogenolysis include Cbz and allyloxycarbonyl. The phthalimide protecting group is typically removed by treatment with hydrazine.

In a preferred embodiment, R$^1$ is substituted at the terminal carbon (i.e., the one bound to the N(1) ring nitrogen) with oxo, making R$^1$ an acyl-containing moiety. More preferred is when R$^1$ contains both the protected amine substituent and the oxo substituent. One of the most preferred R$^1$ groups is:

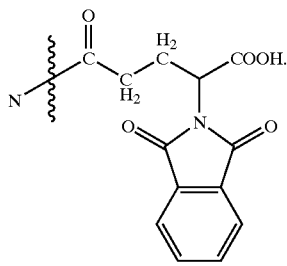

In another preferred embodiment, n is 1.
In yet another preferred embodiment, R$^2$ is t-butyl.
The method of this invention comprises the steps of:
(a) combining compound G with an organic solvent selected from dichloroethane, dichloromethane, toluene, chlorobenzene, chloroform, monoglyme, diglyme, THF, or CCl$_4$;
(b) adding less than about 0.2 equivalents of DMF;
(c) adjusting the temperature of the resulting mixture to between 20° C. and 100° C.;
(d) adding about 2 or more equivalents of SOCl$_2$ to said mixture over a period of between 2 and 24 hours.

Not all organic solvents may be used in step (a). The list of solvents set forth above are known to work. Other similar organic solvents may also work in the reaction and are to be considered part of the present invention. Preferably, the organic solvent is toluene or dichloroethane.

In step (b), it is preferred to use about 0.1 equivalent of DMF. Step (c) is preferably carried out at about 60° C. In step (d), it is preferred to use about 2 equivalents of SOCl$_2$ as a solution in toluene or dichloroethane. It is also preferred that the solution of SOCl$_2$ be added slowly over a period of about 2 hours. Addition of the SOCl$_2$ solution over less than 2 hours tends to drastically reduce the efficiency of the reaction.

According to another preferred embodiment, about 5 equivalents of base are added to the reaction at step (b). Preferably, the base is selected from pyridine, collidine, lutidine, NaHCO$_3$, imidazole, triethylamine, N-methylmorpholine, diisopropylethylamine or K$_2$CO$_3$. Most preferably, the base is 2,6-lutidine.

Once the SOCl$_2$ solution has been added, the reaction is complete. At that point compound H may be isolated by standard procedures, such as diluting the reaction with an organic solvent and then washing the solution first with NaHCO$_3$ and then with brine, followed by drying over Na$_2$SO$_4$ and concentrating.

The conversion of compound G to compound H requires cyclization to occur at the N(2) position. This reaction is seemingly amenable to standard conditions well known in the art for forming an acid chloride intermediate. However, we determined that treating compound G with the known acid chloride forming reagents PCl$_5$, oxalyl chloride, and SOCl$_2$ under conditions well known in the art formed little or no desired product H.

Such well known reaction conditions include combining the starting compound with solvent, typically dichloromethane, and adding 1 equivalent or more of the acid chloride forming reagent (e.g. SOCl$_2$, PCl$_5$, or oxalyl chloride) at various temperatures. The details of the conditions used for some of these reactions are set forth in the examples. Such standard conditions were ineffective in converting compound G to desired compound H. Without being bound by theory, we believe that the method of converting compound G to compound H as set forth herein does not proceed via an acid chloride intermediate.

Extensive experimentation was required to achieve the reaction conditions of this invention. The results of these experiments were highly variable and yields varied greatly depending upon the specific conditions used. Only the method of this invention achieved the conversion of compound G to compound H in high yield (>75%) and purity.

Compound G may be obtained through standard synthetic routes well-known in the art. One such route is depicted below. Scheme 1 depicts the creation of intermediate E.

Scheme 1

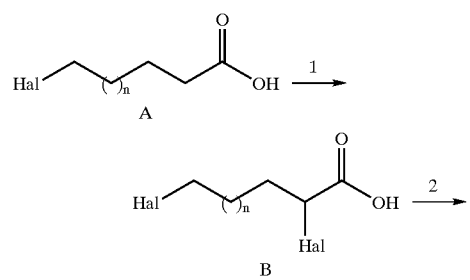

-continued

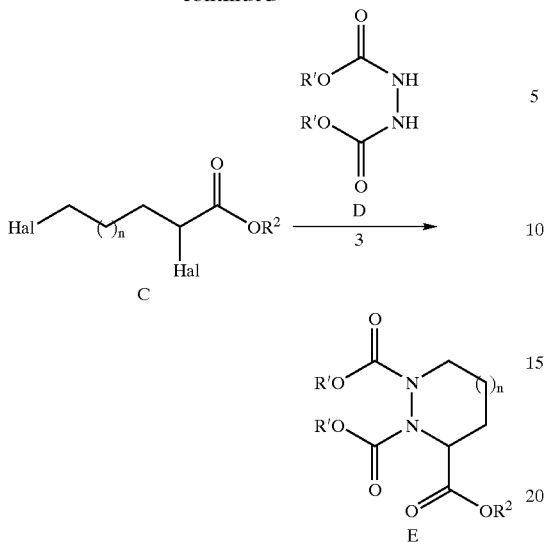

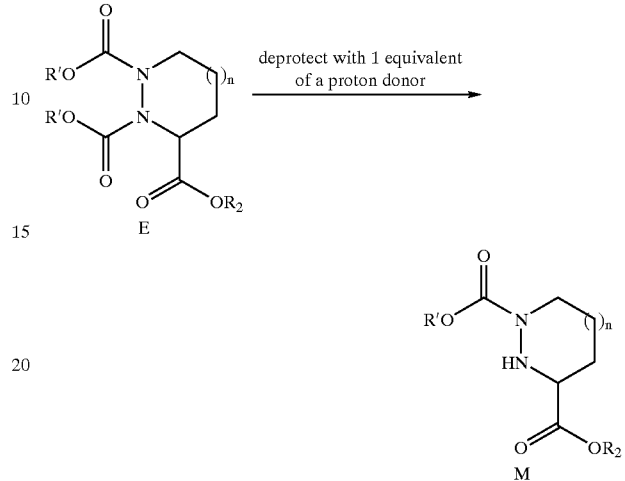

In Scheme 1, "Hal" is any halogen; n and $R^2$ are as defined above; and each R' is an independently selected carboxyl protecting group. Examples of suitable R' include, but are not limited to, alkyl, alkenyl, aryl, and aralkyl groups. Each of these steps is well-known in the art. Specifics concerning the conditions and reagents used at each step are set forth in the Examples.

The conversion of intermediate E to compound G is set forth in Scheme 2, below. That conversion may be achieved in either one of the two ways depicted in Scheme 2, depending upon the nature of $R^1$.

Scheme 2

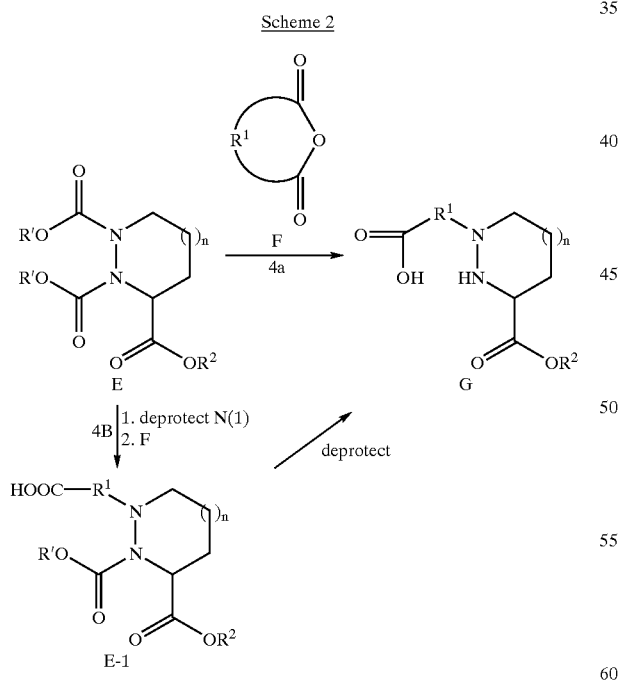

In Scheme 2, R', $R^1$, and $R^2$ are as defined above. Reaction 4A comprises simultaneous deprotection of E and acylation if the amine protecting groups can be removed by hydrogenolysis, e.g., if the protecting group is Cbz. If not, a deprotection step must precede the addition of the anhydride F for the acylation reaction.

In order to completely deprotect at both nitrogens under transfer hydrogenation conditions, at least 2 equivalents of a proton donor (e.g., $Et_3SiH$) must be added. If only one equivalent of the proton donor is added, deprotection occurs selectively at the N(2) nitrogen:

The resulting N(1) protected compound, M, is also useful as an intermediate in producing medically important compounds, such as the ICE inhibitors described herein and in PCT publications WO 97/22619 and WO 95/35308. Thus, this reaction to produce an N(1) protected compound is also an embodiment of the present invention.

When compound F contains substituents and is not symmetrical, reaction 4A may produce mixtures of compounds, wherein acylation of the N(1) nitrogen may occur at either C(O) functionality. This may be avoided by using substituents that favor the formation of the desired product. For example, in reaction 4A, the use of:

as compound F directs the formation of a compound wherein acylation of the N(1) nitrogen occurs at the C(O) functionality furthest away from the phthalimide substituent [J. A. Elberling, et al, *Organic Preparations and Procedures Int.,* pp. 67–70 (1978)].

Reaction 4B depicts the formation of G from intermediate E in a stepwise manner. The two carboxy protecting groups (R') on compound E may be different, such that the N(1) protecting group (—COOR') can be selectively removed without removing the N(2) protecting group. Compound F can then be coupled at the N(1) position to afford compound E-1. Deprotection of the carboxyl protecting group affords compound G. Each of these steps is well known in the art. Specifics concerning the conditions and reagents used at each step are set forth in the Examples.

Intermediate compound G, and its subsequent conversion to compound H, may serve as the key intermediate and synthesis step, respectively, in an improvement in the synthesis of known caspase inhibitors, particularly inhibitors of interleukin-1β converting enzyme ("ICE"), such as those described in U.S. Pat. Nos. 5,716,929, 5,656,627, and 5,756,466 and in PCT publications WO 95/35308 and WO 97/22619.

Those inhibitors have the general formula (I):

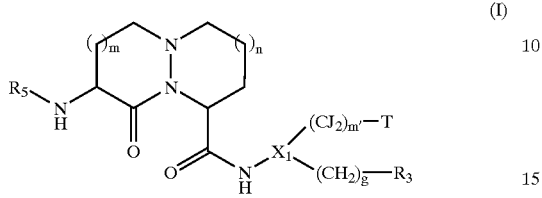

wherein:
any ring is optionally substituted at any carbon by $Q_1$, at any nitrogen by $R_5$, and at any atom by =O, —OH, —COOH, or halogen;
$X_1$ is CH or N;
g is 0 or 1;
m and m' are independently 0, 1 or 2;
n is 0 or 1;
each J is independently selected from —H, —OH, or —F, provided that when a first and a second J are bound to a C, and said first J is —OH, then said second J is —H;
T is —$Ar_3$, —OH, —$CF_3$, —C(O)—C(O)—OH, —C(O)—OH or any biosteric replacement for —C(O)—OH;
$R_3$ is —CN, —CH=CH—$R_9$, CH=N—O—$R_9$, —$(CH_2)_{1-3}$—$T_1$—$R_9$, —$CJ_2$—$R_9$, —C(O)—$R_{13}$, or —C(O)—C(O)—N($R_5$)($R_{10}$);
$T_1$ is —CH=CH—, —O—, —S—, —SO—, —$SO_2$—, —$NR_{10}$—, —$NR_{10}$—C(O)—, —C(O)—, —O—C(O)—, —C(O)—O—, —C(O)—$NR_{10}$—, O—C(O)—$NR_{10}$—, —$NR_{10}$—C(O)—O—, —$NR_{10}$—C(O)—$NR_{10}$—, —$S(O)_2$—$NR_{10}$—, —$NR_{10}$—$S(O)_2$— or —$NR_{10}$—$S(O)_2$—$NR_{10}$—;
each $R_5$ is independently selected from —H, —$Ar_1$, —C(O)—$Ar_1$, —$S(O)_2$—$Ar_1$, —$R_9$, —C(O)—$NH_2$, —$S(O)_2$—$NH_2$, —C(O)—$R_9$, —C(O)—O—$R_9$, —$S(O)_2$—$R_9$, —C(O)—N($R_{10}$)($Ar_1$), —$S(O)_2$—N($R_{10}$)($Ar_1$), —C(O)—N($R_{10}$)($R_9$), or —$S(O)_2$—N($R_{10}$)($R_9$);
each $R_9$ is a $C_{1-6}$ straight or branched alkyl group optionally singly or multiply substituted with —OH, —F, =O or $Ar_1$, wherein any $R_9$ may be substituted with a maximum of two $Ar_1$;
each $R_{10}$ is independently selected from —H or $C_{1-6}$ straight or branched alkyl;
$R_{13}$ is —H, —$Ar_1$, —$R_9$, —$T_1$—$R_9$ or —$(CH_2)_{1-3}$—$T_1$—$R_9$;
each $Ar_1$ is a cyclic group independently selected from a monocyclic, bicyclic or tricyclic aryl group containing 6, 10, 12 or 14 carbon atoms; a monocyclic, bicyclic or tricyclic cycloalkyl group containing between 3 and 15 carbon atoms, said cycloalkyl group being optionally benzofused; or a monocyclic, bicyclic or tricyclic heterocycle group containing between 5 and 15 ring atoms and at least one heteroatom group selected from —O—, —S—, —SO—, —$SO_2$—, =N—, or —NH—, wherein said heterocycle group optionally contains one or more double bonds and optionally comprises one or more aromatic rings;

$Ar_3$ is a cyclic group selected from phenyl, a 5-membered heteroaromatic ring or a 6-membered heteroaromatic ring, wherein said heteroaromatic rings comprise from 1–3 heteroatom groups selected from —O—, —S—, —SO—, —$SO_2$—, =N—, or —NH—;
wherein each $Ar_1$ or $Ar_3$ is optionally singly or multiply substituted at any ring atom by —$NH_2$, —C(O)—OH, —Cl, —F, —Br, —I, —$NO_2$, —CN, =O, —OH, -perfluoro $C_{1-3}$ alkyl,

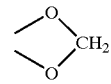

or —$Q_1$; and
each $Q_1$ is independently selected from —$Ar_1$, —$R_9$, —$T_1$—$R_9$, or $(CH_2)_{1-3}$—$T_1$—$R_9$; provided that when —$Ar_1$ is substituted with a $Q_1$ which comprises one or more additional —$Ar_1$ groups, said additional —$Ar_1$ groups are not substituted with $Q_1$.

Preferably, the process of this invention is used as a step in the synthesis of a compound of formula I, wherein n is 1 and m is 2.

In another preferred embodiment, the process of this invention is used as a step in the synthesis of a compound of formula I, wherein $R_5$ is an acyl moiety selected from —C(O)—$Ar_1$, —C(O)—$NH_2$, —C(O)—$R_9$, —C(O)—O—$R_9$, —C(O)—N($R_{10}$)($Ar_1$), or —C(O)—N($R_{10}$)($R_9$).

In yet another preferred embodiment, the process of this invention is used as a step in the synthesis of a compound of formula I, wherein $X_1$ is CH; each J is H; m' is 1; T is —COOH or a biosteric replacement for —COOH; g is 0; and $R_3$ is —C(O)—$R_{13}$.

In the most preferred embodiment of using the process of this invention as a step in the synthesis of a compound of formula I, said compound has the structure:

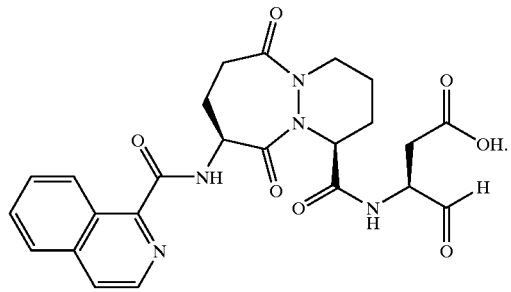

Alternatively, the process of this invention may be used as a step in the synthesis of a compound of the formula (II):

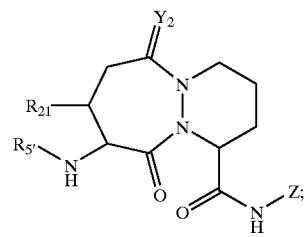

wherein:

Z is selected from

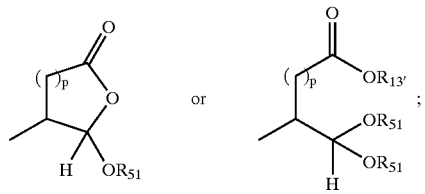

p is 1 or 2;

each $R_{5'}$ is independently selected from —C(O)—$R_{10'}$, —C(O)O—$R_{9'}$, —C(O)—N($R_{10'}$)($R_{10'}$), —S(O)$_2$—$R_{9'}$, —S(O)$_2$—NH—$R_{10'}$, —C(O)—CH$_2$—O—$R_{9'}$, —C(O)C(O)—$R_{10'}$, —$R_{9'}$, —H, —C(O)C(O)—O$R_{10'}$, or —C(O)C(O)—N($R_{9'}$)($R_{10'}$);

each $R_{9'}$ is independently selected from —$Ar_1$ or a —$C_{1-6}$ straight or branched alkyl group optionally substituted with $Ar_1$, wherein the —$C_{1-6}$ alkyl group is optionally unsaturated;

each $R_{10'}$ is independently selected from —H, —$Ar_1$, a —$C_{3-6}$ cycloalkyl group, or a —$C_{1-6}$ straight or branched alkyl group optionally substituted with $Ar_3$, wherein the —$C_{1-6}$ alkyl group is optionally unsaturated;

$R_{13'}$ is selected from H, $Ar_1$, or a $C_{1-6}$ straight or branched alkyl group optionally substituted with $Ar_1$, —CONH$_2$, —O$R_{5'}$, —OH, —O$R_{9'}$, or —CO$_2$H;

each $R_{51}$ is independently selected from $R_{9'}$, —C(O)—$R_{9'}$, —C(O)—N(H)—$R_{9'}$, or two $R_{51}$ taken together form a saturated 4–8 member carbocyclic ring or heterocyclic ring containing —O—, —S—, or —NH—;

each $R_{21}$ is independently selected from —H or a —$C_{1-6}$ straight or branched alkyl group;

$Y_2$ is —H$_2$ or =O each $Ar_1$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by —$Q_1$;

each $Q_1$ is independently selected from the group consisting of —NH$_2$, —CO$_2$H, —Cl, —F, —Br, —I, —NO$_2$, —CN, =O, —OH, -perfluoro $C_{1-3}$ alkyl, $R_{5'}$, —O$R_{5'}$, —NH$R_{5'}$, O$R_{9'}$, —N($R_{9'}$)($R_{10'}$), $R_{9'}$, —C(O)—$R_{10'}$, and

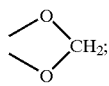

provided that when —$Ar_1$ is substituted with a $Q_1$ group which comprises one or more additional —$Ar_1$ groups, said additional —$Ar_1$ groups are not substituted with another —$Ar_1$.

Preferably, the process of this invention is used as a step in the synthesis of a compound of formula II, wherein $Y_2$ is O and $R_{21}$ is H.

In another preferred embodiment, the process of this invention is used as a step in the synthesis of a compound of formula II, wherein $R_{5'}$ is selected from —C(O)—$R_{10'}$, —C(O)O—$R_{9'}$, —C(O)—N($R_{10'}$)($R_{10'}$), —C(O)—CH$_2$—O—$R_{9'}$, —C(O)C(O)—$R_{10'}$, —C(O)C(O)—O$R_{10'}$, or —C(O)C(O)—N($R_{9'}$)($R_{10'}$).

In yet another preferred embodiment, the process of this invention is used as a step in the synthesis of a compound of formula II, wherein Z is

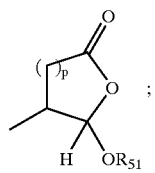

p is 1 and $R_{51}$ is selected from —$Ar_1$, —$C_{1-6}$ straight or branched alkyl or —$C_{1-6}$ straight or branched alkyl substituted with $Ar_1$.

In the most preferred embodiment of using the process of this invention as a step in the synthesis of a compound of formula II, said compound has the structure:

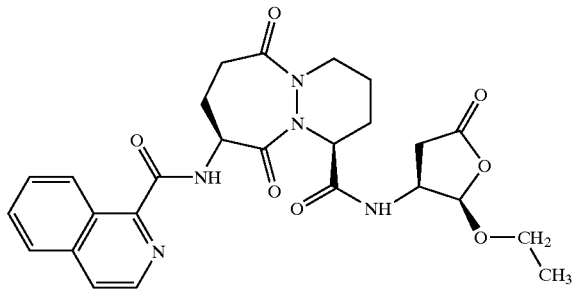

In the synthesis of these inhibitors, $R^1$ contains an amino protecting substituent. Preferably $R^1$ is

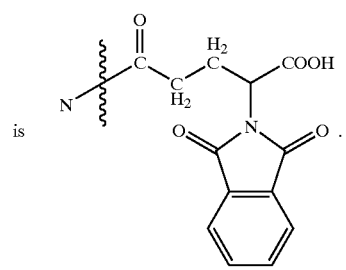

The conversion of compound G to compounds of formula I or II is set forth in Scheme 3 below.

Scheme 3

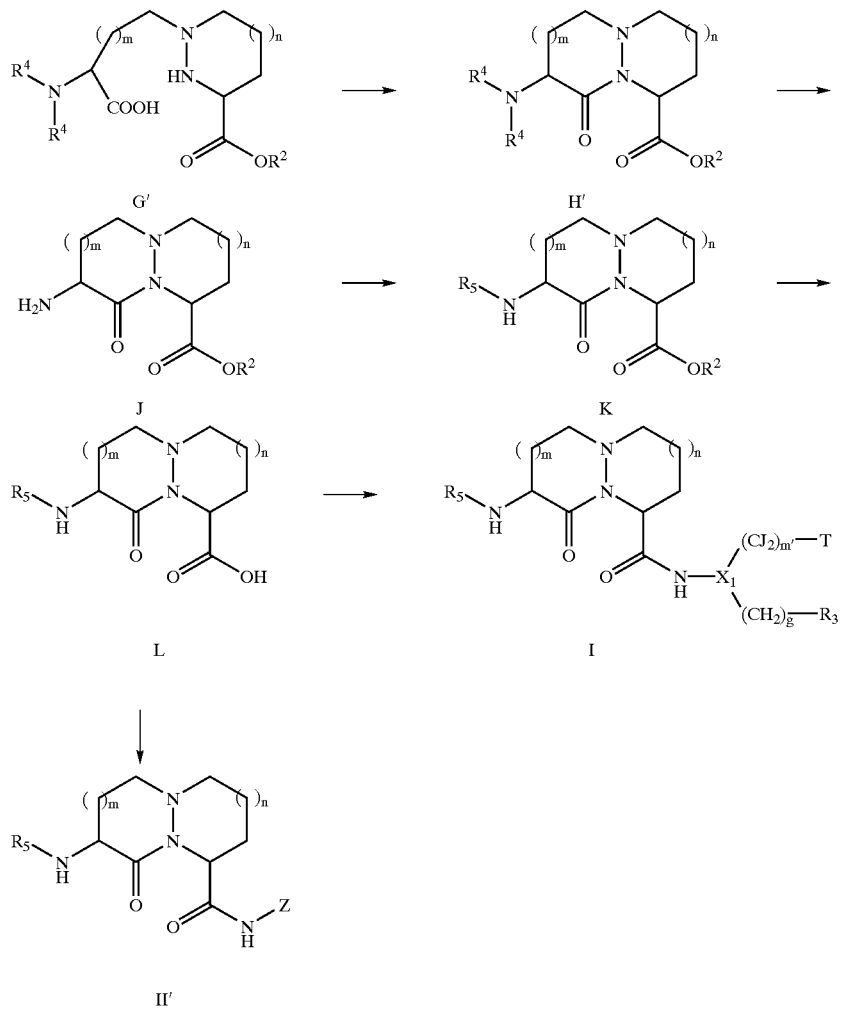

In Scheme 3, $R^2$–$R^5$ C, g, J, m, m', n, $X_1$, Z, and T are as defined above. G' is optionally substituted at any ring carbon with one or more substituents selected from $C_{1-6}$ straight or branched alkyl, $C_{2-4}$ straight or branched alkenyl or alkynyl, O—[$C_{1-6}$ straight or branched alkyl], O—[$C_{2-6}$ straight or branched alkenyl or alkynyl], oxo, halo or $Q_1$;

Each of these steps is well known in the art. Compounds of formula J may be readily obtained from compound H' by deprotection of the amine. When $R^1$ is

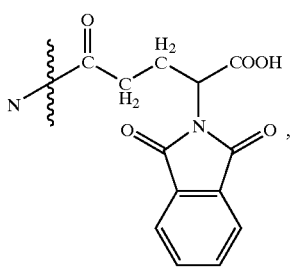

the removal of the amine protecting substituent is typically carried out with hydrazine. Coupling of amine J to $R^5$ is achieved with standard coupling reagents, such as EDC, DCC or acid chloride to afford compound K.

Depending upon the nature of $R^2$, its hydrolysis may be achieved with an acid (when $R^2$ is t-butyl), a hydroxide (when $R^2$ is any other alkyl, alkenyl, alkynyl, or Ar) or hydrogenolysis (when $R^2$ is an Ar-substituted alkyl, alkenyl or alkynyl). This produces the corresponding acid L from the ester K.

The acid L is then coupled using standard coupling conditions to the amine

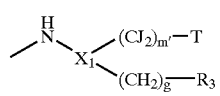

to afford a compound of formula I or to the amine —NH—Z to afford a compound of formula II. These standard coupling conditions include, but are not limited to, EDC, DCC, or acid chloride-mediated coupling.

According to another embodiment, the invention provides a process for converting a compound of formula G to a compound of formula I or II comprising the steps of:
 a) combining compound G with an organic solvent selected from dichloroethane, dichloromethane, toluene, chlorobenzene, chloroform, monoglyme, diglyme, THF, or $CCl_4$;

b) adding less than about 0.2 equivalents of DMF;
c) adjusting the temperature of the resulting mixture to between 20° C. and 100° C.;
d) adding about 2 or more equivalents of SOCl$_2$ to said mixture over a period of between 2 and 24 hours;
e) removing of the amine protecting group from compound H to form amine J;
f) coupling of R$^5$ to amine J to form ester K;
g) deprotecting ester K to form acid L; and
h) coupling acid L to:
   i)

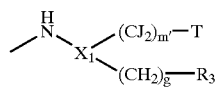

to form a compound of formula I; and
   ii) —NH—Z to form a compound of formula II.

In order that this invention be more fully understood, the following examples are set forth. These examples are for the purpose of illustration only and are not to be construed as limiting the scope of the invention in any way.

EXAMPLES

A. Synthesis of a 7,6 Scaffold for a Caspase Inhibitor

Example 1

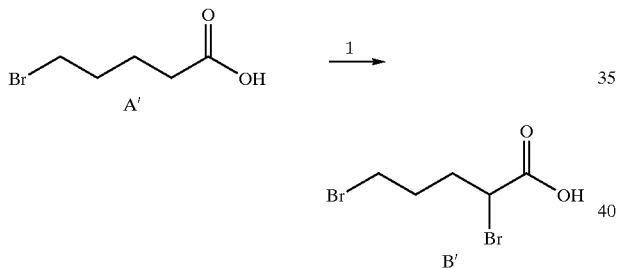

2,5-Dibromovaleric acid: Compound A' was dissolved in 5 equivalents of SOCl$_2$ and then heated to 80° C. for 1 hour. The solution was then cooled to 50° C. and 2 equivalents of bromine were added. The solution was incubated at 50° C. for an additional 12 hours until the red color disappeared. We then cooled the solution to 10° C. and added 4 volumes of water. The solution was then re-heated to 50° C. for another hour. We then separated the organic and aqueous layer, washed the organic layer consecutively with water, Na$_2$SO$_3$ and then brine, removing the aqueous layer after each washing. The final organic layer was then isolated, dried over Na$_2$SO$_4$ and concentrated to produce compound B' as an amber oil.

Example 2

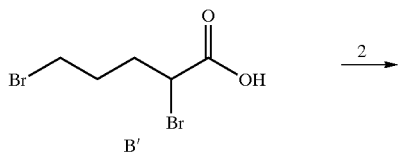

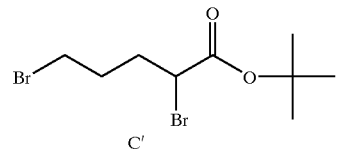

tert-Butyl-(2,5-dibromo)-valerate: Compound B' was treated with 1 equivalent of tert-butanol and 0.1 equivalents of 4-(dimethylamino)-pyridine in a solution of toluene and the resulting solution cooled to 7° C. We then added a solution of 1 equivalent of DCC in toluene while maintaining reaction temperature at less than 22° C. The cooling bath was removed and the reaction was stirred at ambient temperature under a nitrogen atmosphere for 16 hours. The reaction mixture was then diluted with hexane and cooled to 9° C. The resulting solids were removed by filtration. The filtrate was washed consecutively with 0.1N HCl, water, and then sodium bicarbonate. The filtrate was then dried over sodium sulfate and concentrated in vacuo to afford compound C' as a yellow oil.

Example 3

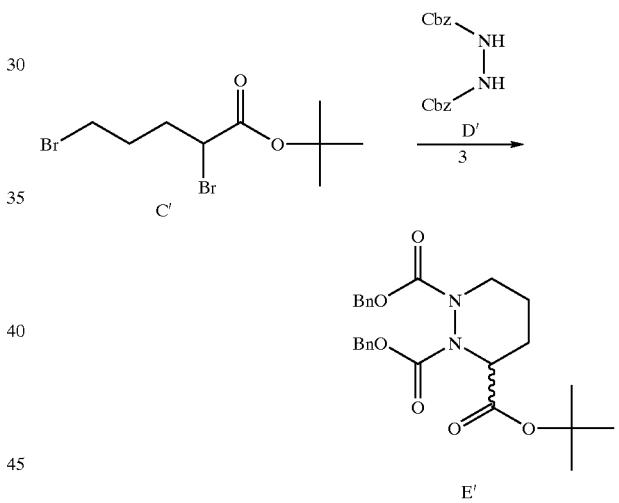

tert-Butyl(N1,N2-bis-benzyloxycarbonyl)-tetrahydropiperazate: Compound D' was combined with 1.2 equivalents of compound C' and dissolved in DMF at ambient temperature under nitrogen atmosphere. We then added granular, anhydrous sodium sulfate, 2.5 equivalents of LiOH monohydrate, and then 0.1 equivalents Bu$_4$NI to the resulting solution. The reaction temperature was maintained at between 20° C. and 30° C. and allowed to stir for 16 hours. The reaction mixture was then diluted with ethyl acetate and water and the layers separated. The organic layer was washed with water and then brine, dried over sodium sulfate and concentrated in vacuo to produce an amber oil. This oil was then dissolved in 5 volumes of ethanol at ambient temperature. We then added 2.5 volumes of water. The resulting mixture was allowed to stir until a white solid formed (approximately 5 hours). The crystallized product was isolated via filtration then dried in vacuo to afford compound E' as a white solid.

Example 4

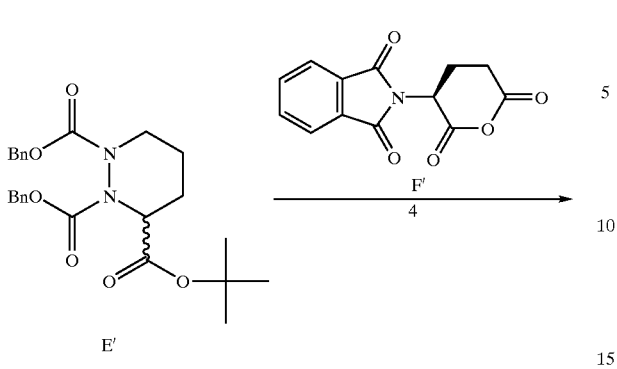

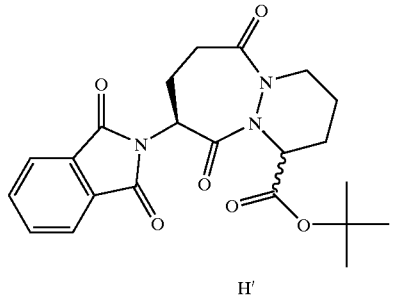

1-(4-Carboxy-4-phthalimido-butyryl)-hexahydropyridazine-3-carboxylic acid tert-butyl ester: We dissolved compound E' in THF. We then added, at ambient temperature under a nitrogen atmosphere, 0.02 equivalents of triethylamine and 0.01 equivalents of Pd(OAc)$_2$. A solution of 2.5 equivalents of triethylsilane (Et$_3$SiH) in THF was then added and the resulting black solution was allowed to stir for 16 hours to complete the reaction. We then added a saturated, aqueous solution of sodium bicarbonate followed by a solution of compound F' in THF. After 30 minutes, the layers were separated and the aqueous layer acidified to pH 4.5 with aqueous citric acid. The product in the aqueous layer was then extracted into ethyl acetate. The organic layer was isolated, washed with brine, dried over sodium sulfate and concentrated in vacuo to produce a white foam. This crude product was then recrystallized from MTBE to afford compound G' as a white powder.

Example 5

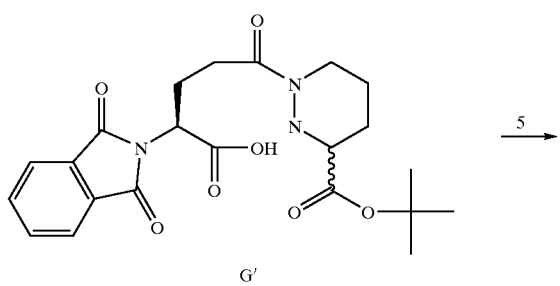

t-Butyl-9-phthalimido-6,10-dioxo-1,2,3,4,7,8,9,10-octahydro-6-H-pyridazino[1,2-a][1,2]diazepine-1-carboxylate: To a suspension of compound G' in dichloroethane was added 0.1 equivalent of DMF. The resulting mixture was heated to 60° C. A solution of 2 equivalents SOCl$_2$ in dichloroethane was added slowly over 2 hours. The reaction was then diluted with ethyl acetate and washed consecutively with NaHCO$_3$ and brine. We then dried the organic layer over Na$_2$SO$_4$ and concentrated to afford compound H' which was then recrystallized from ethyl acetate and hexanes to afford a white solid.

B. Use of Intermediate H' to Produce an Inhibitor of ICE

Example 6

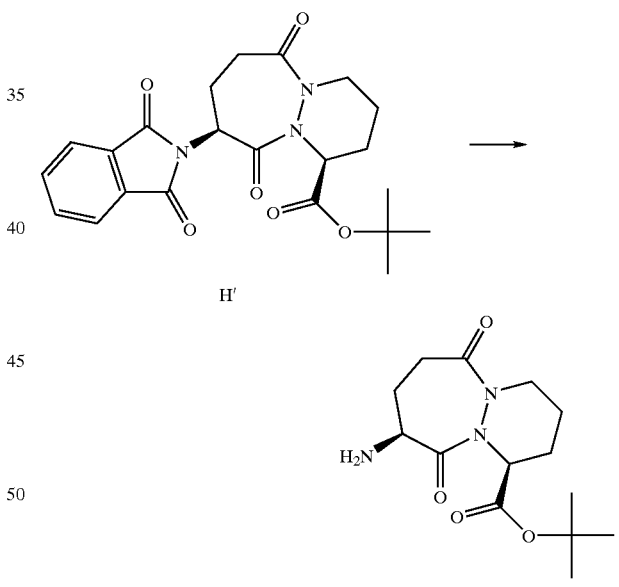

t-Butyl-9-amino-6,10-dioxo-1,2,3,4,7,8,9,10-octahydro-6-H-pyridazino[1,2-a][1,2]diazepine-1-carboxylate (GB 2,128,984): To a suspension of H' (107 g, 0.25 mol) in ethanol (900 mL) was added hydrazine (27 mL, 0.55 mol) and the resulting mixture was allowed to stir at ambient temperature. After 4 hours, the reaction was concentrated in vacuo and the resulting white solid was suspended in acetic acid (1 L of 2N) and allowed to stir at ambient temperature for 16 hours. The resulting white solid was filtered off and washed with water. The filtrate was made basic by the addition of solid sodium carbonate and the product extracted with dichloromethane. The organic layer was washed with brine, dried over magnesium sulfate and concentrated in vacuo to afford 79 g of compound J' as a yellow viscous oil.

Example 7

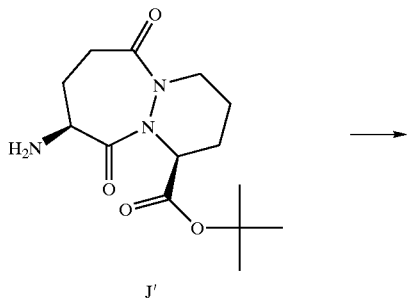

J'

→

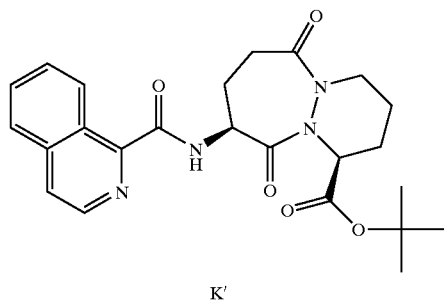

K' t-Butyl-9-(isoquinolin-1-oylamino) -6,10-dioxo-1,2,3,4, 7,8,9,10-octahydro-6-H-pyridazino[1,2-a][1,2]diazepine-1-carboxylate: To a solution of the amine J' (79 g, 0.265 mol) and isoquinolin-1-carboxylic acid (56 g, 0.32 mol) in dichloromethane:DMF (400 mL:400 mL) was added hydroxybenztriazole (54 g, 0.4 mol) and 1-(3-dimethylaminopropyl)-3-ethylcarbodiimide hydrochloride (74 g, 0.39 mol) and the resulting mixture was allowed to stir at ambient temperature for 16 hours. The reaction mixture was poured into water and extracted with ethyl acetate. The ethyl acetate layer was washed with 0.5N sodium bisulfate, water, sodium bicarbonate, brine, dried over sodium sulfate and concentrated in vacuo to afford 122 g of compound K' as an orange solid-foam.

Example 8

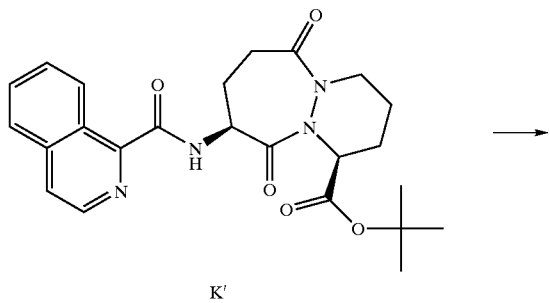

K'

→

-continued

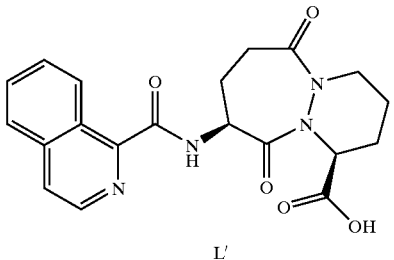

L'

9-(isoquinolin-1-oylamino)-6,10-dioxo-1,2,3,4,7,8,9,10-octahydro-6-H-pyridazino[1,2-a][1,2]diazepine-1-carboxylate: A solution of the ester K' (122 g) in dichloromethane and trifluoroacetic acid (200 mL) was allowed to stir at ambient temperature for 16 hours. The reaction mixture was concentrated to a black oil which was then triturated with acetonitrile and ether to afford 98 g of compound L' as a pale yellow solid.

Example 9

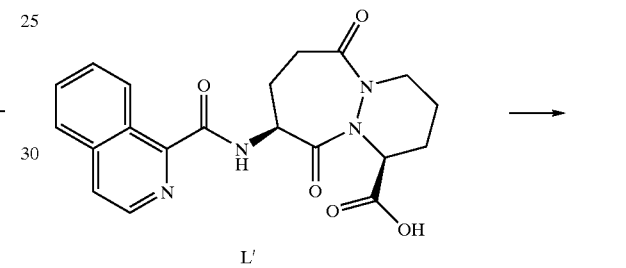

L'

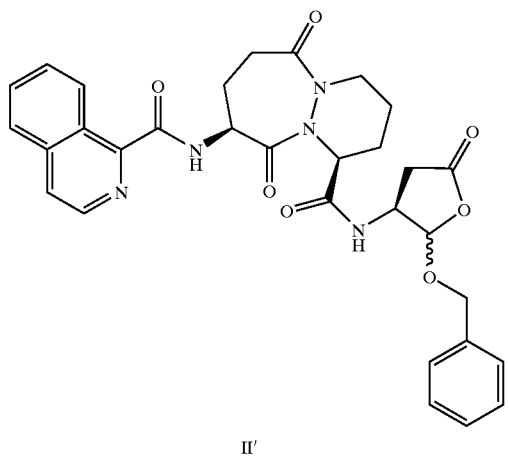

II'

[1S,9S(2RS,3S)]N-(2-benzyloxy-5-oxotetrahydrofuran-3-yl)-6,10-dioxo-9-(isoquinolin-1-oylamino)-1,2,3,4,7,8,9, 10-octahydro-6-H-pyridazino[1,2-a][1,2]diazepine-1-carboxamide: To a solution of (3S,2RS) 3-allyloxycarbonylamino-2-benzyloxy-5-oxotetrahydrofuran [*Bioorg. & Med. Chem. Lett.*, 2, pp. 615–618 (1992)] (4.4 g, 15.1 mmol) in dichloromethane was added N,N-dimethylbarbituric acid (5.9 g, 3.8 mmol) then tetrakispalladium(0) triphenyl phosphine (1.7 g, 1.5 mmol) and the resulting mixture was allowed to stir at ambient temperature for 15 minutes. To the resulting mixture was added the acid, compound L' (5.0 g, 12.6 mmol), hydroxybenztriazole(2.0 g, 14.8 mmol) then 1-(3-dimethylaminopropyl)-3-ethylcarbodiimide hydrochloride (2.7 g, 14 mmol) and the reaction was allowed to stir for 3 hours at ambient temperature. The reaction mixture was then poured into water and extracted with ethyl acetate. The organics were washed with 0.5M sodium bisulfate, water, sodium bicarbonate, brine, dried over magnesium sulfate and concentrated in vacuo to afford 2.6 g of the crude product as a yellow foam. The crude material was purified by column chromatography (SiO$_2$, dichloromethane:acetone 9:1–3:1) to afford 1.2 g of the compound II'.

Compound II' and related compounds that may be synthesized using the method of this invention as an intermediate step are described in WO 97/22619, the disclosure of which is herein incorporated by reference. Those related compounds may be synthesized from the product of the method of this invention, H or H', through modifications of the procedure set forth in Examples 6 through 9. Such modifications are well known in the art.

C. Experiments for the Conversion of Compound G' to H' Using Standard Acyl Chloride Forming Conditions The conversion of compound G' to compound H' was not effected, or poorly effected, by the use of standard acid chloride forming conditions known to one of ordinary skill in the art. Such conditions are exemplified in Examples 10 through 13 hereinbelow.

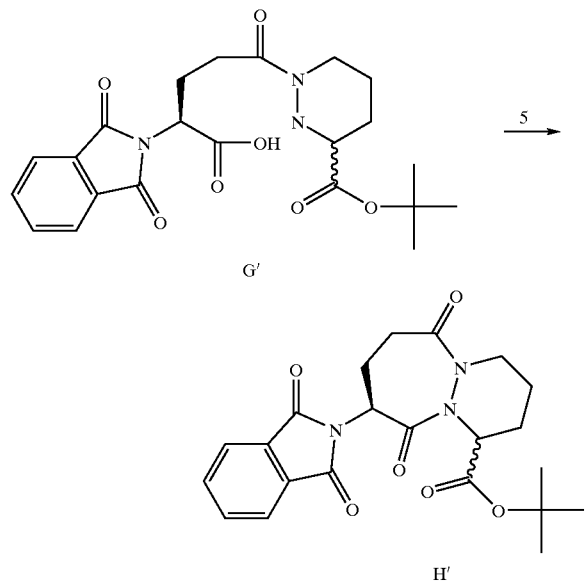

Example 10

Oxalyl chloride (1 equiv) was added to a mixture of compound G' and DMF (catalytic amount) in dichloromethane at room temperature. After 10 minutes, a sample of the reaction mixture was removed and analyzed by HPLC (Microsorb C18-reverse phase column; 0→100% MeCN (0.1% TFA); 20 minutes; 40° C.; 214 nm). Only a trace amount of product was observed by HPLC analysis. We then added DBU (2 equivalents) to the reaction mixture and heated to 40° C. The reaction was monitored over time by HPLC analysis. No reaction was observed.

Example 11

Oxalyl chloride (1 equiv) was added to a mixture of compound G' and DMF (catalytic amount) in dichloromethane at room temperature. The reaction was heated to 40° C. After 30 minutes, a sample of the reaction mixture was removed for analysis. When no reaction was observed by HPLC analysis (using the conditions set for the in Example 10), more oxalyl chloride was added (1 equiv) and the reaction continued at 40° C. The reaction was monitored over a 2 hour time period by HPLC analysis. No reaction was observed.

Example 12

To a mixture of compound G' in dichloromethane, at room temperature, was added PCl$_5$ (1.25 equiv). The reaction was allowed to stir for 15 minutes then NaHCO$_3$ (saturated, aqueous) was added. The reaction was monitored over time by HPLC analysis. No reaction was observed.

Example 13

To a mixture of compound G' and DMF (0.05 equiv) in dichloromethane, at room temperature, was added SOCl$_2$ (4 equiv). The resulting reaction mixture was then heated at 40° C. After 2 hours, a sample of the reaction mixture was removed for HPLC analysis. A small amount desired product H was formed as determined by HPLC. After 18 hours, the reaction was diluted with ethyl acetate, washed with NaHCO$_3$ and concentrated in vacuo. The crude product was purified by column chromatography (SiO$_2$, dichloromethane:EtOAc 19:1→4:1)to afford compound H' in 22% yield.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A process for producing a compound of formula (I):

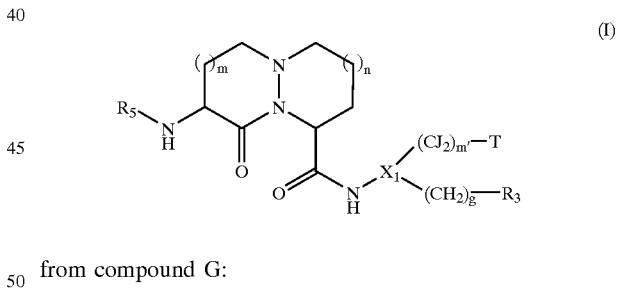

from compound G:

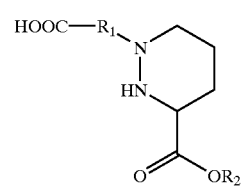

wherein:

any ring is optionally substituted at any carbon by Q$_1$, at any nitrogen by R$_5$, and at any atom by =O, —OH, —COOH, or halogen;

X$_1$ is CH or N;

g is 0 or 1;

m is 0, 1 or 2;

n is 0 or 1;

each J is independently selected from —H, —OH, or —F, provided that when a first and a second J are bound to a C, and said first J is —OH, then said second J is —H;

T is —$Ar_3$, —OH, —$CF_3$, —C(O)—C(O)—OH, —C(O)—OH or any biosteric replacement for —C(O)—OH;

$R_3$ is —CN, —CH=CH—$R_9$, CH=N—O—$R_9$, —$(CH_2)_{1-3}$—$T_1$—$R_9$, —$CJ_2$—$R_9$, —C(O)—$R_{13}$, or —C(O)—C(O)—N($R_5$)($R_{10}$);

$T_1$ is —CH=CH—, —O—, —S—, —SO—, —$SO_2$—, —$NR_{10}$—, —$NR_{10}$—C(O)—, —C(O)—, —O—C(O)—, —C(O)—O—, —C(O)—$NR_{10}$—, O—C(O)—$NR_{10}$—, —$NR_{10}$—C(O)—O—, —$NR_{10}$—C(O)—$NR_{10}$—, —$S(O)_2$—$NR_{10}$—, —$NR_{10}$—$S(O)_2$— or —$NR_{10}$—$S(O)_2$—$NR_{10}$—;

each $R_5$ is independently selected from —H, —$Ar_1$, —C(O)—$Ar_1$, —$S(O)_2$—$Ar_1$, —$R_9$, —C(O)—$NH_2$, —$S(O)_2$—$NH_2$, —C(O)—$R_9$, —C(O)—O—$R_9$, —$S(O)_2$—$R_9$, —C(O)—N($R_{10}$)($Ar_1$), —$S(O)_2$—N($R_{10}$)($Ar_1$), —C(O)—N($R_{10}$)($R_9$), or —$S(O)_2$—N($R_{10}$)($R_9$);

each $R_9$ is a $C_{1-6}$ straight or branched alkyl group optionally singly or multiply substituted with —OH, —F, =O or $Ar_1$, wherein any $R_9$ may be substituted with a maximum of two $Ar_1$;

each $R_{10}$ is independently selected from —H or $C_{1-6}$ straight or branched alkyl;

$R_{13}$ is —H, —$Ar_1$, —$R_9$, —$T_1$—$R_9$ or —$(CH_2)_{1-3}$—$T_1$—$R_9$;

each $Ar_1$ is a cyclic group independently selected from a monocyclic, bicyclic or tricyclic aryl group containing 6, 10, 12 or 14 carbon atoms; a monocyclic, bicyclic or tricyclic cycloalkyl group containing between 3 and 15 carbon atoms, said cycloalkyl group being optionally benzofused; or a monocyclic, bicyclic or tricyclic heterocycle group containing between 5 and 15 ring atoms and at least one heteroatom group selected from —O—, —S—, —SO—, —$SO_2$—, =N—, or —NH—, wherein said heterocycle group optionally contains one or more double bonds and optionally comprises one or more aromatic rings;

$Ar_3$ is a cyclic group selected from phenyl, a 5-membered heteroaromatic ring or a 6-membered heteroaromatic ring, wherein said heteroaromatic rings comprise from 1–3 heteroatom groups selected from —O—, —S—, —SO—, —$SO_2$—, =N—, or —NH—;

wherein each $Ar_1$ or $Ar_3$ is optionally singly or multiply substituted at any ring atom by —$NH_2$, —C(O)—OH, —Cl, —F, —Br, —I, —$NO_2$, —CN, =O, —OH, -perfluoro $C_{1-3}$ alkyl,

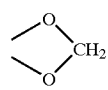

or —$Q_1$; and each $Q_1$ is independently selected from —$Ar_1$, —$R_9$, —$T_1$—$R_9$, or $(CH_2)_{1-3}$—$T_1$—$R_9$; provided that when —$Ar_1$ is substituted with a $Q_1$ which comprises one or more additional —$Ar_1$ groups, said additional —$Ar_1$ groups are not substituted with $Q_1$; said process comprising the steps of:

a) combining compound G with an organic solvent selected from dichloroethane, dichloromethane, toluene, chlorobenzene, chloroform, monoglyme, diglyme, THF, or $CCl_4$;

b) adding less than about 0.2 equivalents of DMF;

c) adjusting the temperature of the resulting mixture to between 20° C. and 100° C.;

d) adding about 2 or more equivalents of $SOCl_2$ to said mixture over a period of between 2 and 24 hours;

e) removing the amine protecting group from compound H:

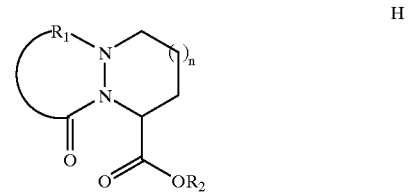

to form amine J:

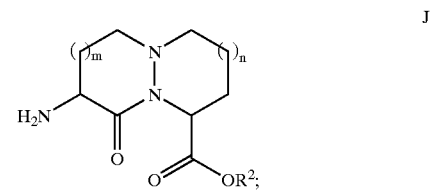

f) coupling of $R^5$ to amine J to form ester K:

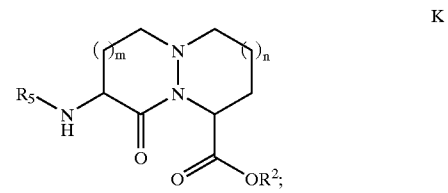

g) deprotecting ester K to form acid L:

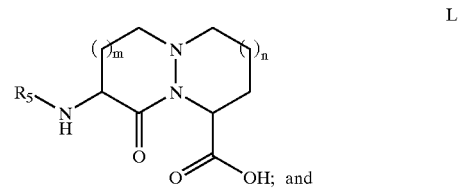

h) coupling acid L to

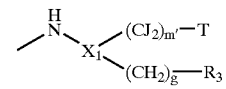

to form the compound of formula I.

2. The process according to claim 1, wherein m is 2 and n is 1.

3. The process according to claim 2, wherein the terminal $R_5$ is selected from —C(O)—$Ar_1$, —C(O)—$NH_2$, —C(O)—$R_9$, —C(O)—O—$R_9$, —C(O)—N($R_{10}$)($Ar_1$), or —C(O)—N($R_{10}$)($R_9$).

4. The process according to claim 3, wherein:

X$_1$ is CH;

each J is H;

m' is 1;

T is —COOH or a biosteric replacement for —COOH;

g is 0; and

R$_3$ is —C(O)—R$_{13}$.

5. The process according to claim 4, wherein compound I has the structure:

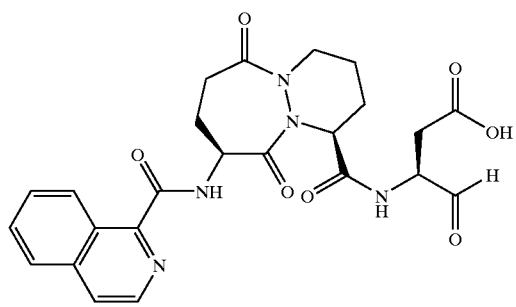

6. A process for producing a compound of formula (II):

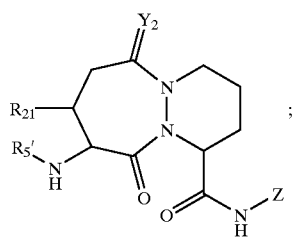

(II)

from compound G:

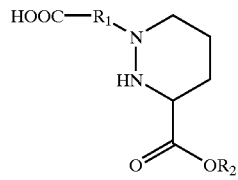

G wherein:

Z is selected from

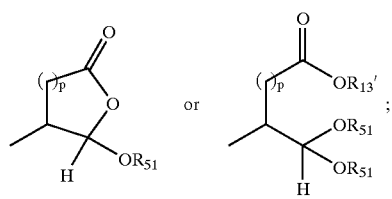

p is 1 or 2;

each R$_{5'}$ is independently selected from —C(O)—R$_{10'}$, —C(O)O—R$_{9'}$, —C(O)—N(R$_{10'}$)(R$_{10'}$), —S(O)$_2$—R$_{9'}$, —S(O)$_2$—NH—R$_{10'}$, —C(O)—CH$_2$—O—R$_{9'}$, —C(O)C(O)—R$_{10'}$, —R$_{9'}$, —H, —C(O)C(O)—OR$_{10'}$, or —C(O)C(O)—N(R$_{9'}$)(R$_{10'}$);

each R$_{9'}$ is independently selected from —Ar$_1$ or a —C$_{1-6}$ straight or branched alkyl group optionally substituted with Ar$_1$, wherein the —C$_{1-6}$ alkyl group is optionally unsaturated;

each R$_{10'}$ is independently selected from —H, —Ar$_1$, a —C$_{3-6}$ cycloalkyl group, or a —C$_{1-6}$ straight or branched alkyl group optionally substituted with Ar$_3'$, wherein the —C$_{1-6}$ alkyl group is optionally unsaturated;

R$_{13'}$ is selected from H, Ar$_1$, or a C$_{1-6}$ straight or branched alkyl group optionally substituted with Ar$_1$, —CONH$_2$, —OR$_{5'}$, —OH, —OR$_{9'}$, or —CO$_2$H;

each R$_{51}$ is independently selected from R$_{9'}$, —C(O)—R$_{9'}$, —C(O)—N(H)—R$_{9'}$, or two R$_{51}$ taken together form a saturated 4–8 member carbocyclic ring or heterocyclic ring containing —O—, —S—, or —NH—;

each R$_{21}$ is independently selected from —H or a —C$_{1-6}$ straight or branched alkyl group;

Y$_2$ is —H$_2$ or =O each Ar$_1$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by —Q$_1$; and each Q$_1$ is independently selected from the group consisting of —NH$_2$, —CO$_2$H, —Cl, —F, —Br, —I, —NO$_2$, —CN, =O, —OH, -perfluoro C$_{1-3}$ alkyl, R$_{5'}$, —OR$_{5'}$, —NHR$_{5'}$, OR$_{9'}$, —N(R$_{9'}$)(R$_{10'}$), R$_{9'}$, —C(O)—R$_{10'}$, and

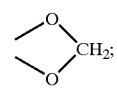

provided that when —Ar$_1$ is substituted with a Q$_1$ group which comprises one or more additional —Ar$_1$ groups, said additional —Ar$_1$ groups are not substituted with another —Ar$_1$, said process comprising the steps of:

a) combining compound G with an organic solvent selected from dichloroethane, dichloromethane, toluene, chlorobenzene, chloroform, monoglyme, diglyme, THF, or CCl$_4$;

b) adding less than about 0.2 equivalents of DMF;

c) adjusting the temperature of the resulting mixture to between 20° C. and 100° C.;

d) adding about 2 or more equivalents of SOCl$_2$ to said mixture over a period of between 2 and 24 hours;

e) removing the amine protecting group from compound H:

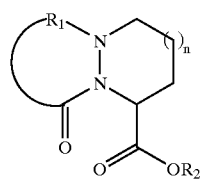

H to form amine J:

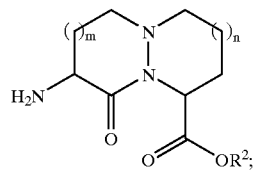

J f) coupling of $R^5$ to amine J to form ester K:

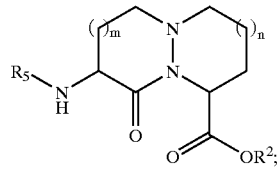

K g) deprotecting ester K to form acid L:

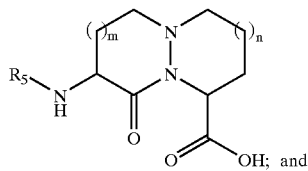

L h) coupling acid L to —NH—Z to form the compound of formula II.

7. The process according to claim 6, wherein in compound II, $Y_2$ is O and $R_{21}$ is H.

8. The process according to claim 7, wherein in compound II, $R_{5'}$ is selected from —C(O)—$R_{10'}$, —C(O)O—$R_{9'}$, —C(O)—N($R_{10'}$)($R_{10'}$), —C(O)—CH$_2$—O—$R_{9'}$, —C(O)C(O)—$R_{10'}$, —C(O)C(O)—O$R_{10'}$, or —C(O)C(O)—N($R_{9'}$)($R_{10'}$).

9. The process according to claim 8, wherein in compound II,

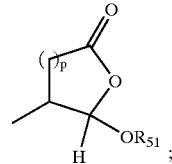

Z is H p is 1; and $R_{51}$ is selected from —$Ar_1$, —$C_{1-6}$ straight or branched alkyl or —$C_{1-6}$ straight or branched alkyl substituted with $Ar_1$.

10. The process according to claim 9, wherein compound II has the structure:

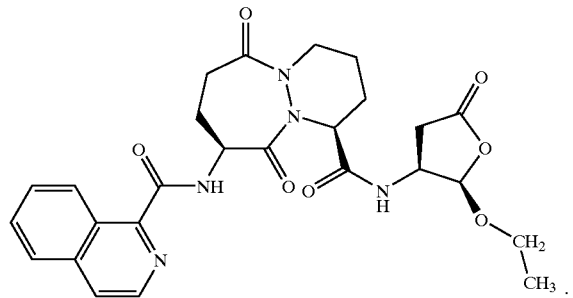

* * * * *